(12) United States Patent
Pawlak

(10) Patent No.: US 9,290,426 B2
(45) Date of Patent: Mar. 22, 2016

(54) METHOD OF MAKING OXYGENATES FROM A NON-CATALYTIC CHEMICAL REACTION

(71) Applicant: Nathan Pawlak, Charlevoix, MI (US)

(72) Inventor: Nathan Pawlak, Charlevoix, MI (US)

(73) Assignee: Stranded Solutions, LLC, Charlevoix, MI (US)

( * ) Notice: Subject to any disclaimer, the term of this patent is extended or adjusted under 35 U.S.C. 154(b) by 0 days.

(21) Appl. No.: 14/399,547

(22) PCT Filed: May 9, 2013

(86) PCT No.: PCT/US2013/040455
§ 371 (c)(1),
(2) Date: Nov. 7, 2014

(87) PCT Pub. No.: WO2013/170106
PCT Pub. Date: Nov. 14, 2013

(65) Prior Publication Data
US 2015/0133703 A1 May 14, 2015

Related U.S. Application Data

(60) Provisional application No. 61/644,782, filed on May 9, 2012.

(51) Int. Cl.
*C07C 29/50* (2006.01)
*C07C 27/14* (2006.01)
*B01J 8/18* (2006.01)

(52) U.S. Cl.
CPC ............... *C07C 29/50* (2013.01); *B01J 8/1836* (2013.01); *C07C 27/14* (2013.01); *B01J 2208/0038* (2013.01)

(58) Field of Classification Search
CPC ........................................................ C07C 29/50
See application file for complete search history.

(56) References Cited

U.S. PATENT DOCUMENTS

| | | | |
|---|---|---|---|
| 2,836,902 A | 6/1958 | North | |
| 3,006,944 A | 10/1961 | Fenske et al. | |
| 4,263,448 A * | 4/1981 | Leacock | 560/246 |
| 4,618,732 A * | 10/1986 | Gesser et al. | 568/910.5 |
| 4,896,631 A | 1/1990 | Holm et al. | |
| 4,982,023 A * | 1/1991 | Han et al. | 568/910.5 |
| 6,025,403 A | 2/2000 | Marler et al. | |
| 2007/0100005 A1 | 5/2007 | Pawlak et al. | |
| 2009/0118553 A1 | 5/2009 | Pawlak et al. | |
| 2011/0000406 A1 | 1/2011 | Eriksson et al. | |
| 2011/0232795 A1 | 9/2011 | Hardin | |

OTHER PUBLICATIONS

International Search Report, Three (3) Pages, Dated Nov. 13, 2013.
European Search Report, 16 Pages, Dated Oct. 15, 2015.
Ullman'S Encyclopedia of Industrial Chemistry, "Reactor Types and Their Industrial Applications" vol. B4, pp. 87-120.

\* cited by examiner

*Primary Examiner* — Brian J Davis
(74) *Attorney, Agent, or Firm* — Dickinson Wright PLLC

(57) ABSTRACT

A system and a method for forming oxygenates from a non-catalytic reaction. A hydrocarbon gas and an oxygen-containing gas are fed into a mixer and then heated to form a reactant gas stream. The reactant gas stream is fed into a fluidized bed reactor where the reaction of the gases occurs by oxidization to produce oxygenates. The oxygenate products are then removed from the reactor.

42 Claims, 8 Drawing Sheets

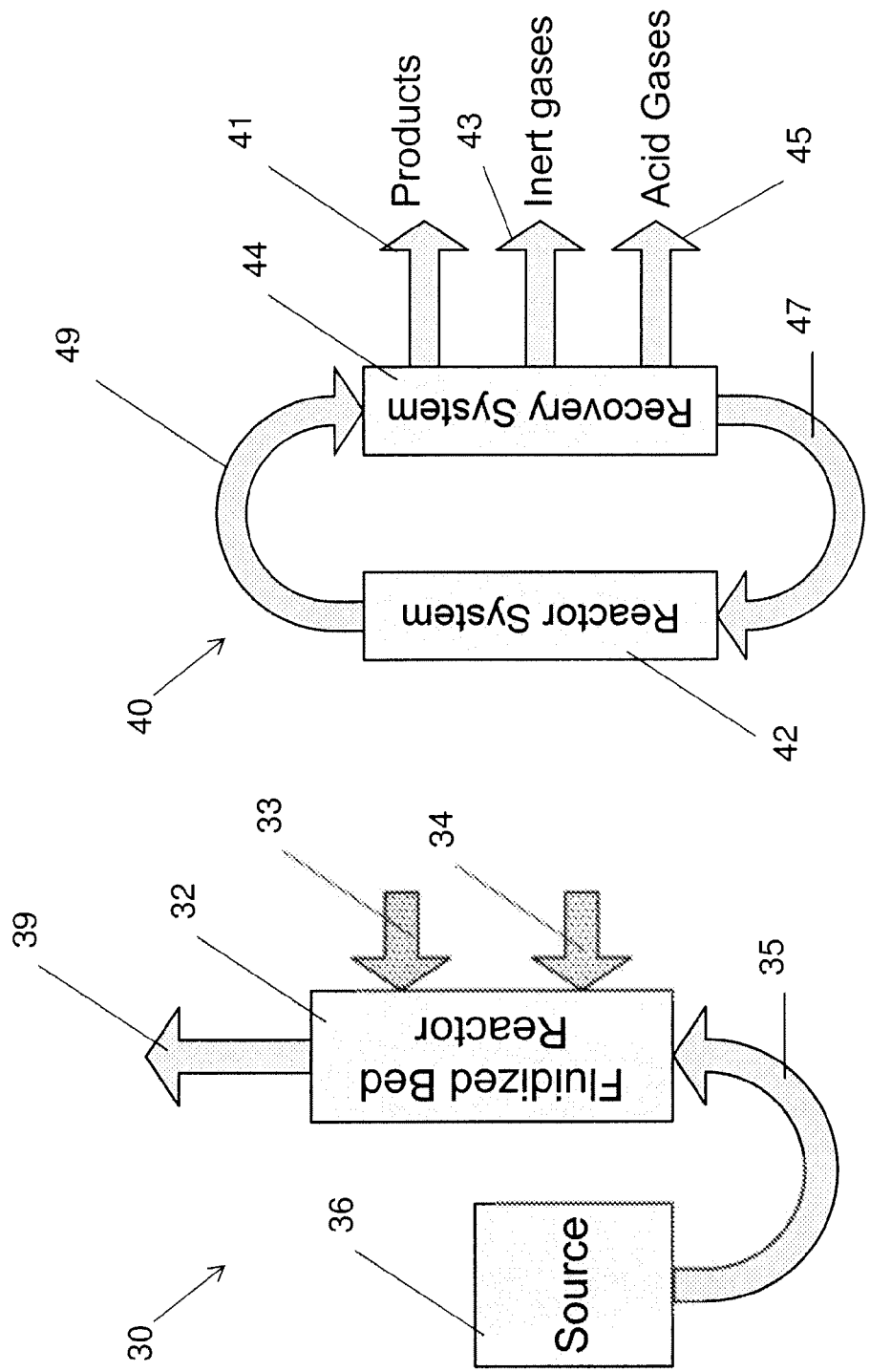

METHOD OF MAKING OXYGENATES FROM A NON-CATALYTIC CHEMICAL REACTION

CROSS REFERENCE TO RELATED APPLICATION

This application is a National Stage application of International Application No. PCT/US2013/040455, filed May 9, 2013, which claims the benefit of U.S. Provisional Patent Application Ser. No. 61/644,782 filed May 9, 2012, entitled "System And Method Of Making Oxygenates In Fluidized Bed," the entire disclosures of these applications being considered part of the disclosure of this application and hereby incorporated by reference.

BACKGROUND OF THE INVENTION

1. Field of the Invention

The present invention relates to a method of making oxygenates, particularly a method of making oxygenates from a non-catalytic chemical reaction.

2. Description of the Prior Art

Natural gas is an abundant fossil fuel resource. The composition of natural gas at the wellhead varies but the majority of the hydrocarbon contained in the natural gas is methane. Other constituents of natural gas may include ethane, propane, butanes, pentane, and heavier hydrocarbons.

A reaction which has been extensively studied for many years is the direct partial oxidation reaction of the hydrocarbons in natural gas, particularly methane and ethane, to oxygenates, e.g. methanol, and ethanol, however, care must be taken to avoid oxidation to formaldehyde or other undesirable deep oxidation reactions including CO and $CO_2$. The mechanism of alcohol formation is believed to involve a radical reaction, e.g. methyl free radicals and hydroxyl free radicals. Unfortunately, the per pass yield to valuable oxygenates has been limited, making these systems uneconomical. This limited yield has been rationalized as resulting from the low reactivity of C—H bonds in the hydrocarbons, e.g., methane, in relation to the higher reactivity of the primary oxygenated product, e.g. methanol, which results in selectivity formation of the highly undesirable deep oxidation products CO and $CO_2$ when attempts are made to increase conversion.

A variety of reaction systems and methods for conversion of hydrocarbons to desirable oxygenates through direct partial oxidation of the hydrocarbons are known; however each of those reaction systems has significant problems that have prevented these systems from being used to recover gas at location where it would normally be flared due to lack of infrastructure to capture the natural gas. Since the direct partial oxidation reaction of hydrocarbons to oxygenates is exothermic in nature, tubular reactors that carry out the direct partial oxidation reaction often develop "hot spots" and are difficult to efficiently control. Accordingly, it is very problematic to keep the reaction temperature constant inside the reactor. In addition, since the direct partial oxidation reaction of hydrocarbons to oxygenates is a gas phase reaction, heat integration between gas reactants and gas products require gas to gas heat exchange. Gas to gas heat exchange is notoriously inefficient because there are infrequent collisions between the gas particles and the walls of the heat exchanger. Therefore, for direct partial oxidation reaction of hydrocarbons to oxygenates, heat transfer becomes a limiting factor in process design. The implementation of hydrocarbon gas conversion has been limited to complex plants with substantial infrastructure and controls, which are not possible in remote locations.

SUMMARY AND ADVANTAGES OF THE INVENTION

The present invention relates to a method of making oxygenates, particularly a method of making oxygenates from a non-catalytic chemical reaction.

A method for making oxygenates from a non-catalytic reaction including the steps of mixing a first stream of hydrocarbon gas with a second stream of gas including oxygen in a mixer and outputting a reactant stream from the mixer including the hydrocarbon gas of the first stream and the second stream of gas including oxygen. The reactant stream is heated to a predetermined temperature range and the heated reactant stream is inputted into the fluidized bed reactor, wherein the fluidized bed reactor includes a reaction chamber, a plurality of inert reactor particles in the reaction chamber. Of course the pressure and temperature ranges may vary relative to each other, such that as pressure increases the temperature range may be lowered. The heated reactant stream is input into the reaction chamber of the fluidized bed reactor. Typically, the heated reactant stream enters the reactor from the bottom, or against gravity and then passes through a distributor plate including a plurality of holes. The holes may be arranged in a ring patter, with a plurality of rings, each including a plurality of holes. As the gas enters the reactor and passes through the distributor plate, inert reactor particles in the reaction chamber or input into the reaction chamber from above, or on the opposite side of the distributor plate from the point of entry of the heated reactant stream into the reaction chamber are fluidized. More specifically, fluidizing the inert reactor particles in the reaction chamber occurs by feeding the heated reactant stream vertically through the reaction chamber and suspending the inert reactor particles in the reaction chamber of the fluidized bed reactor. The reaction of the gases in the reactant stream occurs by oxidizing in the reaction chamber of the fluidized bed reactor the hydrocarbon gas in the heated reactant stream with the gas including oxygen in the heated reactant stream to produce oxygenates. As the reactor includes an optimal isothermal reaction, a control system is used for maintaining the fluidized bed reactor at or substantially at an isothermal condition. Substantially at isothermal reaction means as close as possible to an isothermal condition, such as within 10% of isothermal condition, preferably within 5% of isothermal condition and more preferably within 2.5% of isothermal condition. Of course, it is desirable to have the reaction at a substantially isothermal condition of within 1% or less. The reactor generally has a desired operating temperature range and even in cases where the isothermal condition is not maintained within preferences of 10%, higher conversion rates can be achieved as temperature rise is dampened. The reactor also generally has an operating pressure of at least 40 atm to facilitate the production of the oxygenates. Upon oxidation, the method may include the step of outputting a product stream including the oxygenates, byproducts, and unreacted hydrocarbon gas from the fluidized bed reactor.

The method may further include a heat exchanger having a first portion and a second portion and wherein the second portion is at least partially located in the reaction chamber and wherein the heated reactant stream is directly fed to the fluidized bed reactor from the first portion of the heat exchanger at a temperature of at least 300° C. In addition, it is preferable that at a point of entry into the fluidized bed reactor, the temperature is at least 300° C. for reaction with methane, although for a reactor primarily focused on ethane gas it may be 5-20% less.

The method further includes a step of cycling a coolant between the first portion of the heat exchanger and a second portion of the heat exchanger allowing the fluidized bed reactor to complete the step of heating and further as part of the step of heating, perform a step of cooling the fluidized bed reactor with minimal energy expenditure as part of the step of maintaining the fluidized bed reactor at an isothermal condition. As the reaction is an exothermic reaction, removal of heat to preheat the gas is both desirable and energy efficient.

The heated reactant stream exiting the first portion of the heat exchanger includes a plurality of inert particles and further includes the step of removing the plurality of inert particles from the reactant stream before the reactant stream enters the reactor. The method step of step of removing the plurality of inert particles from the heated reactant stream occurs by transferring the heated reactant stream through a particle separator to separate the inert particles from the heated reactant stream, before the reactant stream enters the fluidized bed reactor. The step of inputting the inert particles removed from the heated reactant stream by the particle separator into the reaction chamber of the fluidized bed reactor, on an opposite side of the distributor plate from the point of entry of the reactant stream into the reactor chamber. The method may also include the step of inputting the inert particles to cool the reaction chamber. The method may also include a step of transferring the inert particles from the reaction chamber of the first fluidized bed reactor to the heat exchange, and wherein such a step of transferring the inert particles from the reaction chamber heats the first portion of the heat exchanger.

The method may include a step of accelerating the heated reactant stream having a first velocity before the first portion of the heat exchanger and a second velocity in the first portion of the heat exchanger in the heat exchanger. The step of accelerating the heated reactant stream in the heat exchanger may also include the step of maintaining the first velocity with the heated reactant stream and wherein the heated reactant stream is forced through a reduced diameter section in the first portion of the heat exchanger to increase the first velocity of the reactant stream to the second velocity that is greater than the first velocity.

The method may include a step of cycling a coolant between the first portion and the second portion of the heat exchanger to heat the first portion of the heat exchanger and to cool the second portion in the reaction chamber.

The method may include a step of isolating the oxygenates in the product stream from the byproducts and the unreacted hydrocarbon gas by feeding the product stream through a first recovery system that separates the product stream into oxygenates and a recycle stream including the byproduct and the unreacted hydrocarbon gas. The recycle stream is substantially free of oxygenates. Of course, the reactant stream and recycle stream may be passed through the reactor multiple times because the conversion rate may be as low as 5% for each pass through the reactor, however it is expected that the system and method of the present invention may convert at least 8% of the hydrocarbons, preferably 10%, more preferably 13% and most preferably at least 15% during each pass. The system may be recycled until the almost all hydrocarbons have been removed, leaving water, oxygenates and byproducts as the primary constituents. Of course, the method may also include a step of removing the byproducts from the recycle stream.

As stated above, the method may include a step of recycling the unreacted hydrocarbon gas from the first recovery system after the step of removing the byproducts from the recycle stream. The recycle stream is input to the fluidized bed reactor and may be input solely with the addition of a gas including oxygen or may be input in combination with a reactant stream including hydrocarbon gas and a gas including oxygen.

The method includes step of inputting the recycle stream to a second fluidized bed reactor having a second reaction chamber and oxidizing the unreacted hydrocarbon gas in the recycle stream in the second reaction chamber of the second fluidized bed reactor to produce oxygenates. The method may include a step of outputting a second product stream from the second fluidized bed reactor wherein the second product stream includes oxygenates, byproducts and unreacted hydrocarbon gas. Of course in regards to the second product stream, the method may include a step of isolating the oxygenates from the second product stream by inputting the second product stream through a second recovery system and separating the oxygenates from the byproduct and the unreacted hydrocarbon gas in the second product stream.

To maintain isothermal reaction and optimal reaction parameters, the pressure of the reactant stream in the step of heating is at a pressure of at least 40 atm, preferably when the reactant stream enters the fluidized bed reactor between 40 atm and 85 atm, and more preferable between 41 atm and 55 atm. Of course, the step of maintaining may also use these same pressures. In further regards to the step of maintaining, a temperature range between 300° C. and 900° C., preferably between 400° C. and 600° C., and more preferably between 426° C. and 483° C. is considered optimal, particularly with regards to methane in the hydrocarbon gas. Of course, it has been found that optimal temperature for ethane may be slightly lower, such as 2-10% lower. Also, in comparison, since the reaction is exothermic, generally the reactant stream in the step of heating is at the predetermined range between 316° C. and 372° C.

The reactor may include a distributor plate having a plurality of apertures disposed on the distributor plate to allow a thorough mixture between the first stream of hydrocarbon gas and the second stream of gas including oxygen. The distributor plate may be fastened to the fluidized bed reactor using fasteners, or may be welded.

The method may also include the steps of feeding a first stream of hydrocarbon gas into a mixer; feeding a recycle stream from a recovery system into the mixer; mixing the first stream and the recycle stream in the mixer to output a combined stream; heating the combined stream to a first predetermined temperature of at least 300° C. by feeding the combined stream through a heat source and wherein the combined stream is fed to the heat source at a pressure of at least 40 atm; inputting the heated combined stream from the heat source into a fluidized bed reactor having a reaction chamber and a plurality of inert reactor particles in the reaction chamber; inputting a second stream of gas including oxygen at a second predetermined temperature which is lower than the first predetermined temperature to the fluidized bed reactor separately from the heated combined stream; controlling the volume of the second stream inputted into the fluidized bed reactor based on the internal temperature of the fluidized bed reactor; distributing the heated reactant stream into the reaction chamber of the fluidized bed reactor by sending the heated reactant stream through a distributor plate; fluidizing the inert reactor particles in the fluidized bed reactor by feeding the heated combined stream and the second stream through the reaction chamber and suspending the inert reactor particles in the reaction chamber of the fluidized bed reactor; oxidizing the hydrocarbon gas in the heated combined stream with the second stream of gas including oxygen in the reaction chamber of the fluidized bed reactor to produce oxygenates; varying the flow rate of the second stream to maintain the fluidized bed reactor at an isothermal condition having an operating temperature between 300° C. and 900° C. and an operating pressure of at least 40 atm to facilitate with the production of the oxygenates; outputting a product stream including the oxygenates, byproducts, and unreacted hydrocarbon gas from the fluidized bed reactor; isolating the oxygenates from the product stream by sending the product stream through the recovery system configured to separate the oxygenates in the product stream from the recycle stream which includes the byproducts and the unreacted hydrocarbon gas; and cycling the byproducts and the unreacted hydrocarbon gas from the product stream by sending the recycle stream to the mixer.

In addition, the method steps may be cycled by sending the recycle stream to the mixer to repeat the process, such as until the amount of hydrocarbon gas is under a desirable level. In addition, step of varying is at the operating temperature may be between 400° C. and 600° C., preferably between 426° C. and 483° C. Likewise, the step of inputting the second stream of gas including oxygen is at the second predetermined temperature between 20° C. and 300° C., preferably at a second predetermined temperature between 30° C. and 120° C., and more preferably at a second predetermined temperature between 38° C. and 93° C.

While the heat source is preferably a heat exchanger, it may be instead a heater, but also may be a combination of a heat exchanger and heater. Of course, upon startup the heat source may easily be a heater as the reaction chamber may not be yet to the desired temperature where it can preheat the reactant stream or gas.

In the method, the combined stream enters the heat source in the step of heating at the pressure between 40 atm and 85 atm, preferably between 41 atm and 55 atm. The reactor may include a distributor plate having a plurality of apertures to allow a thorough mixture between the first stream of hydrocarbon gas and the second stream of gas including oxygen.

The method for making oxygenates from a non-catalytic reaction, the method comprising the steps of compressing a first stream including a hydrocarbons gas to a predetermined pressure of at least 40 atm; heating the compressed first stream to a first predetermined temperature of at least 300° C. by feeding the compressed first stream through a heat source; inputting the heated and compressed first stream directly from the heater into a first reactor having a first reaction chamber; inputting a gas including oxygen at a second predetermined temperature into the first reaction chamber of the first reactor and separately from the heated stream; oxidizing the hydrocarbon gas of the heated and compressed first stream with the second stream of gas including oxygen in the first reaction chamber of the first reactor to produce oxygenates; outputting a product stream including the oxygenates, byproducts and unreacted hydrocarbon gas from the first reactor; isolating the oxygenates from the product stream with a recovery system separating the oxygenates from a recycle stream having the byproducts and the unreacted hydrocarbon gas; inputting the recycle stream into a second reactor having a second reaction chamber; inputting the second stream of gas including oxygen at the second predetermined temperature to the second reactor separately from the recycle stream; oxidizing the unreacted hydrocarbon gas in the recycle stream with the second stream of gas including oxygen in the second reaction chamber of the second reactor to produce oxygenates; outputting a second product stream including the oxygenates, byproducts and unreacted hydrocarbon gas from the second reactor; and isolating the oxygenates from the second product stream with the recovery system separating the oxygenates from the byproducts and the unreacted hydrocarbon gas of the second product stream.

The above method steps are well configured for using the first reactor to remove heavier gases, such as ethane, propane and the like, and may even convert them to some oxygenates along with methane. The methane is then oxidized in the second reactor to oxygenates. The two reactor system is configured to allow optimization for hydrocarbon gasses that are heavier than methane in the first reactor and methane in the second reactor, thereby optimizing the recovery in each of the reactors. As such, typically less recycle streams may need to be used and the conversion rate for the hydrocarbons is at least 8%, preferably at least 10%, more preferably at least 13% and most preferably at least 15% for each pass through at least the second reactor. As the first reactor is primarily directed to hydrocarbon gasses that are not methane, the first reactor may be a non-fluidized reactor and the second reactor may be a fluidized bed reactor including a plurality of inert reactor particles in the second reaction chamber.

The method may further including the step of fluidizing the inert reactor particles in the fluidized bed reactor by feeding the recycle stream and the second stream through the reaction chamber and suspending the inert reactor particles in the second reaction chamber of the second fluidized bed reactor. In addition, the step of isolating the oxygenates from the product stream may include using a first separator of the recovery system and the step of isolating the oxygenates from the second products stream includes using a second separator of the recovery system. The method may include compressing the first stream is compressed to the predetermined pressure between 40 atm and 85 atm, preferably between 41 atm and 55 atm.

In addition, the step of heating the compressed first stream is heated to the first predetermined temperature between 300° C. and 900° C., preferably between 310° C. and 600° C., and more preferably between 316° C. and 372° C.

As the system includes two reactors, the step of inputting the gas including oxygen is at the second predetermined temperature is at least 30° C., preferably between 30° C. and 120° C. and more preferably between 36° C. and 96° C., however the temperature may vary slightly for each reactor, with the first reactor having a lower input temperature. In addition, the system is configured wherein the first reactor operates at a first reactor temperature and a first reactor pressure and the second reactor operates at a second reactor temperature and a second reactor pressure and wherein the first reactor temperature is less than the second reactor temperature. The first reactor may operate at a first reactor temperature and a first reactor pressure and the second reactor operates at a second reactor temperature and a second reactor pressure and wherein the first reactor pressure is less than the second reactor pressure. Of course, the first reactor has a first reaction chamber volume and the second reactor has a second reactor chamber volume and the first reactor chamber volume is smaller than the second reactor chamber volume. A method step of inputting a gas including oxygen in the first reaction chamber further includes the step of feeding the gas including oxygen at a rate to control the pressure and temperature in the reaction chamber of the first reactor to oxidize primarily with ethane, and wherein the step of inputting as including oxygen in the second reaction chamber includes the step of feeding the gas including oxygen at a rate to control the pressure and temperature in the reaction chamber of the second reactor to oxidize primarily with methane.

In regard to the method, as oxygen is added, the overall conversion has been found to increase, however the present system allows such an increase without getting sudden ramps in temperature that instead or producing oxygenates produce undesirable $CO_2$.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 3 is a schematic view showing a third embodiment of the direct partial oxidation reaction system wherein reactants are heated automatically by inert particles carrying heat from the reaction, FIG. 4 is a schematic view showing a recovery system that can be used in connection with the direct partial oxidation reaction system in FIG. 1, FIG. 2 and FIG. 3.

DETAILED DESCRIPTION OF THE ENABLING EMBODIMENTS

Figure 2:
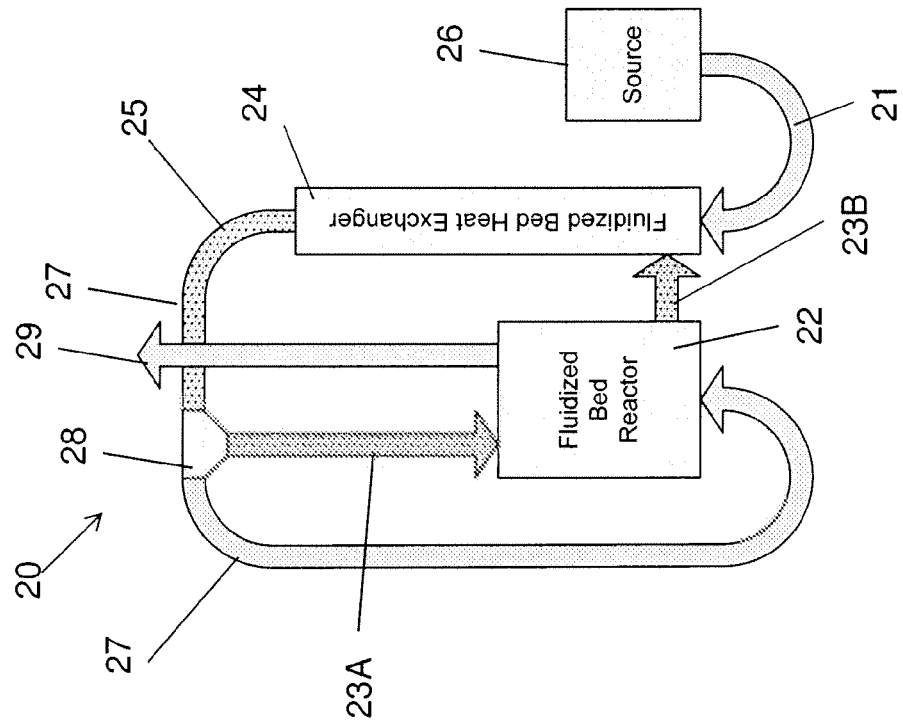
FIG. 2 is a schematic view showing a second embodiment of the direct partial oxidation reaction system with a heat exchanger and a fluidized bed reactor having inert particles moving therebetween as a heat sink for the system.

The present disclosure provides for a system and method of producing oxygenates from hydrocarbons such as alkanes in a gas-phase reaction. The reaction is homogeneous and takes place in a substantially inert fluidized bed reactor. The inert fluidized bed reactor maintains the reactor conditions within a desired temperature range operable to produce the desired oxygenates and allows an isothermal or pseudo-isothermal operating condition. The present invention also uses uniquely configured heat exchanger systems and recycles the reactant and product streams to further facilitate thermal management.

Stranded gas at well heads that is not economically feasible to bring to market is referred to as stranded gas and typically flared. This stranded gas using the present invention may be converted into liquid fuels resulting from reactions in the presence of an inert material/solid. More specifically, gaseous alkanes in the stranded gas may be converted into a variety of liquid oxygenates, such as by combining a hydrocarbon gas source with oxygen-containing gas or air in a fluidized bed reactor. The direct partial oxidation of alkanes leads to the production of a range of liquid oxygenates and the present invention provides a novel way of easily controlling the process. A process according to the present invention utilizes a fluidized bed of inert materials operable to generally maintain isothermal conditions and maximize oxygenate selectivity. As such no catalyst or catalytic reaction is needed. The reactants, specifically the hydrocarbon gas and oxygen containing gas, can be premixed to allow for suitable mixing prior to entering the reactor or even be mixed in the reactor. Premixing allows for more uniform mixing prior to reaction and thus better conversion into desired products, however, as elevated below the control system and method of control may be simplified through inputting oxygen containing gas into the reactor without premixing.

The reactor and, in some instances, a heat exchanger include solid particles are substantially inert and used for thermal transfer. This means that the particles do not contribute significantly to the desired reaction. In addition, inert coatings and inert lining, e.g. quartz lining, glass coating, may be applied to the inner walls of reactors. Some particles considered inert or substantially inert may have surfaces that contribute to reactivity. According to the present disclosure, the particles should allow for the reaction to favor a homogeneous reaction of the reactants. Any degree of heterogeneous reaction is dominated by the homogeneous reaction. In an example, the solid particles allow for a conversion of the reactants to the desired oxygenate formed in a homogenous reaction of 60%, 70%, 80% and 90%, 95%, 98%, 99%, or more. Accordingly, the particles should be substantially non-catalytic.

An example inert solid particle is sand. Sand can behave much like a liquid by mixing with a fluid such as water. In this example, the sand particles are temporarily entrained into the surrounding fluid and take on liquid characteristics until the mixing is stopped and the solids settle out. In much the same way, a gas can flow through a bed of solid particles in an opposite direction of the pull of gravity on the particles. The drag created by the flow of gas pulls on the solid particles. As the velocity of the gas is increased, the drag increases until it is sufficient to overcome the downward pull of gravity. At this point, at least some of the solid particles will become suspended within the gas and behave as a fluid. The suspension of solid particles within the fluid can be referred to as "fluidization." A fluidized bed refers to a vessel or physical unit that allows for this fluid and particle interaction. A fluidized bed reactor refers to such a physical unit in which a reaction takes place. If the particles are inert, i.e., they do not chemically interact with the reactant gases, then the packed bed contains inert solid particles. In the present invention, the inert particles are used to improve heat transfer in the fluidized bed reactor, as further described below.

Some characteristics of a fluidized gas-solid can be similar to characteristics of a liquid system. For instance, the particles may generally assume the shape of the container they occupy. The solid particles can, therefore, be transported as pseudo-liquids as long as the fluidization is maintained. A fluidized system can allow solids to move relatively freely like a liquid. The most preferable particle size for the inert particles of the present invention ranges between 10 μm-500 μm.

Another characteristic of a fluidized gas-solid system is that heat can be transferred effectively between the fluidized medium and fixed solid surfaces such as walls or heat exchanger tubing. Because each inert solid particle is surrounded on all sides by the gas medium, there is much more surface area through which solids can absorb (or release) heat as compared to a system without these particles. Heat transfer efficiency is therefore increased. In a fluidized state, the inert solids will be colliding with their surroundings more often than in a non-fluidized state, thus providing solid-solid contact and greatly increasing heat transfer rates. In fact, if two fluidized beds are in contact with one another, they might have a heat transfer coefficient 5-25 times higher than the heat transfer coefficient of the same system without fluidization.

It has been found in the present invention that use of a fluidized bed allows for more steady temperature increase and even heat distribution as compared to an unfluidized system. The suspended particles can act much like a heat sink for the surrounding fluid. If heat is applied to one end of a fluidized bed reactor, it is distributed through the physical circulation of the suspended material, and as such few significant heat gradients may exist, thus reducing "hot spots" within a fluidized bed reactor. This allows heating or cooling to be applied substantially uniformly to the system and allows the opportunity for what is essentially or at least a controlled approach as close as possible to an isothermal reactor. If almost or as much heat is removed as is produced by a reaction (assisted by the higher heat transfer of the fluidized system), then the entire system from the point the gases enter to the point they exit may essentially be the same. In addition, the heat removed may act to cool the reactor, which includes the exothermic reacting and heat the incoming gases to desired temperature.

The present disclosure provides for direct partial oxidation of alkanes to oxygenates. An alkane is a chemical compound that consists of only hydrogen and carbon having no double or triple bonds. Suitable alkanes include linear or branched unsaturated hydrocarbons, such as with 1 to 10 carbon atoms. The most common and simplest alkane is methane, but ethane, propane, n-butane, i-butane, pentane, hexane, etc. are also alkanes. The bonds are all exclusively either single C—H bonds or single C—C bonds. The addition of oxygen (whether in pure form or diluted, such as in air) to alkanes under elevated pressure and elevated temperature can produce a variety of oxygenates.

Oxygenates are compounds that contain oxygen (e.g., oxygen-containing hydrocarbon derivatives of the above alkanes). The most common oxygenates produced by the reaction of alkanes and oxygen are alcohols, but the reaction can also produce aldehydes, carbon oxides (e.g., carbon monoxides, carbon dioxides), and even some carboxylic acids. Alcohols, aldehydes, and carboxylic acids generally have the same or fewer number of carbon atoms as the alkane from which they are derived. Water is a common byproduct. Consider the following example chemical stoichiometric formulas:

Methane Partial Oxidation $2CH_4 + O_2 \rightarrow 2CH_3OH$ (alcohols)

$CH_4 + O_2 \rightarrow CH_2O + H_2O$ (aldehydes)

$CH_4 + 2O_2 \rightarrow CO_2 + 2H_2O$ or $2CH_4 + 3O_2 \rightarrow 2CO + 4H_2O$ (carbon oxides)

$2CH_4 + 3O_2 \rightarrow 2HCOOH + 2H_2O$ (carboxylic acids)

Ethane Partial Oxidation $CH_3CH_3 + O_2 \rightarrow 2CH_3OH$ or $CH_3CH_3 + O_2 \rightarrow CH_3CH_2OH$ (alcohols)

$2CH_3CH_3 + 3O_2 \rightarrow 4CH_2O + 2H_2O$ or $CH_3CH_3 + O_2 \rightarrow CH_3CHO + H_2O$ (aldehydes)

$2CH_3CH_3 + 7O_2 \rightarrow 4CO_2 + 6H_2O$ or $2CH_3CH_3 + 5O_2 \rightarrow 4CO + 6H_2O$ (oxides)

$2CH_3CH_3 + 5O_2 \rightarrow 4HCOOH + 2_2O$ or $2CH_3CH_3 + O_2 \rightarrow 2CH_3COOH + 2H_2O$ (carboxylic acids)

The results follow a similar pattern with higher alkanes. The major products obtained from the reactions mentioned above are methanol and water. Major side products from the reactions above include $CO_2$, formaldehyde, and ethanol. Several minor side products such as higher alcohols, e.g. propanol, butanol, can also be obtained. A minor pass through chemicals expected are aromatic hydrocarbons such as benzene, however, the amount of the aromatic hydrocarbons is negligible. Similarly, trace amounts of carboxylic acids, higher aldehydes can also be obtained as the minor side product. From the reaction of higher alkanes, methane can be obtained as a minor side product. As with any $CO_2$, water containing system, the formation of carbonic acid must also be made aware of. The direct partial oxidation of alkanes with oxygen under elevated temperatures and pressures using the system and method of the present invention is a commercially viable route for the production of methanol and other oxygenates.

Sources of hydrocarbon reactant can often include a mixture of different types of hydrocarbons. Natural gas for example, which can be obtained from natural gas reserves in the ground, or associated gas, which can be obtained from oil reserves in the ground, will both typically contain a mixture of methane, ethane, and higher hydrocarbons. In a reaction system which reacts a mixed hydrocarbon reactant with an oxidant, the reaction can often favor the higher carbon hydrocarbons for conversion over conversion the lower carbon hydrocarbons. Accordingly, a sequence of reaction and recovery systems can be employed as shown and discussed later in FIG. 6. This series of reaction and recovery systems can also be employed for the purpose of increasing overall product yield, assisting with heat integration, improving overall reaction characteristics, for decreasing the size of the recycle loop of the overall system, or for any other reason. The allowance of $CO_2$ to pass from one reactor to the next can provide additional benefits, particularly in small doses.

Figure 13A:
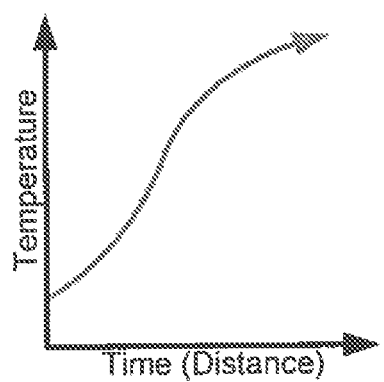
FIG. 13A is a representative temperature curve showing the temperature increase as a function of time and distance across a reactor with direct partial oxidation not in accordance with the present invention.
Figure 13B:
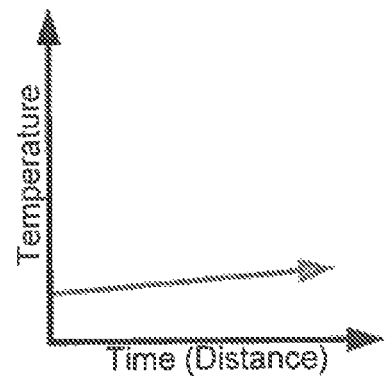
FIG. 13B is a representative temperature curve showing the temperature increase as a function of time and distance across a reactor designed according to the present invention.

The present invention provides for systems and methods of heat and temperature control using fluidization as well as other control systems. Alcohols (most notably methanol) can be a dominant product of a reaction provided that the reactor conditions may be kept relatively constant. The alcohol oxygenate products desirably have high selectivity relative to other reaction products, for example at least about 50% and/or up to about 90%. Traditionally, direct partial oxidation is carried out in a tubular reactor. Since the reaction is highly exothermic and since tubular reactors inherently develop hot spots (per their nature), the oxidant may require significant dilution in order to prevent unacceptable temperature increases and prevent over-oxidation. FIG. 13A is a representative temperature curve showing the temperature increase as a function of time and distance across a reactor, and is typical of a direct partial oxidation, As the gases react along the axial direction of a tubular reactor, the temperature increases. The overall conversion of alkanes from 1-10% can be expected while maintaining acceptable selectivity for alcohols (beyond that higher temperatures move the reaction out of its "sweet spot" resulting in more complete oxidation favoring products such as carbon dioxides over alcohols). A system according to the present disclosure can carry out the same reaction in a fluidized bed reactor where the undesired temperature increase will be reduced. In various embodiments, the steady-state temperature gradient $\Delta T$ expressed as a difference between the reactor outlet and inlet temperature can be at least 1° C., 2° C., 5° C. and or up to 5° C., 10° C., 15° C., or 20° C. In an example, the temperature increase across the reactor will be 5 degrees Celsius or less as represented by the curve shown in FIG. 13B.

Using the fluidized bed of the present invention having particles capable of being fluidized allows for such a desired temperature profile. Accordingly, a reaction system of the present disclosure is not bound to lower conversion percentages by the exothermic nature of the reaction. In various embodiments, the overall alkane feed conversion can be at least about 5 to 10% and/or up to 10% or more, expressed on a molar basis relative to the total alkane fed to the reaction system.

Utilizing direct partial oxidation of alkanes to oxygenates can be hampered by the pre-heating requirements of the reactants. The reaction takes place at elevated temperatures and, therefore, the gases should be heated before entering the reactor. Heat availability is therefore an issue in traditional systems as there is an excess of heat produced by the reaction itself. The present disclosure provides for heat integration to further control heat variation associated with preheating.

Heat integration between gas reactants and gas products can be achieved by gas-gas heat exchange. Gas-gas heat exchange can be inefficient due to the density of gas being such that there are relatively infrequent collisions between the gases and the walls of the heat exchanger as compared to the heat transfer between liquids or solids. The heat exchanger may become a limiting factor in the design of a direct partial oxidation system.

Figure 1:
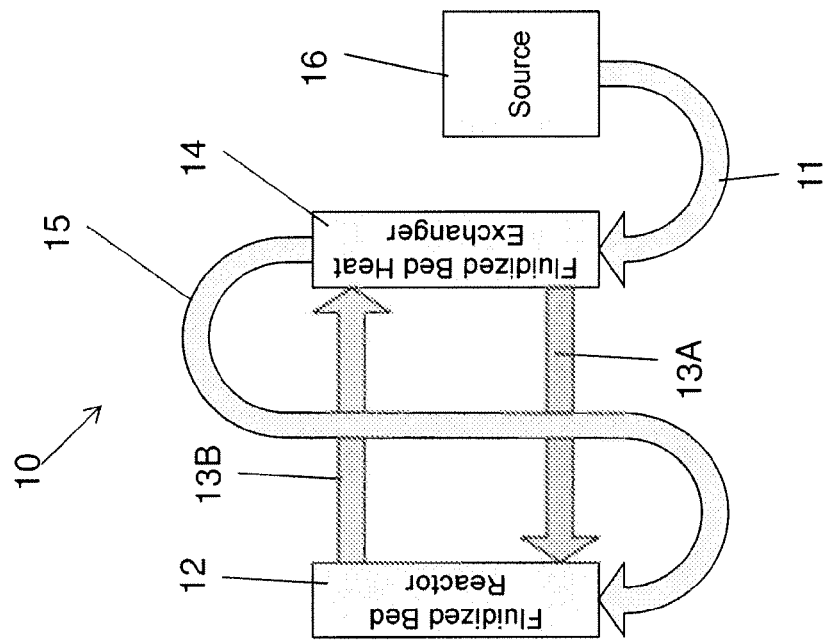
FIG. 1 is a schematic view showing a direct partial oxidation reaction system with a heat exchanger and a fluidized bed reactor having a coolant cycling therebetween.

Referring to FIGS. 1-4, a process according to the present disclosure not only utilizes the advantages of fluidization for the reactor side of a heat exchanger, but for the cool side of the heat exchanger as well. FIG. 1 illustrates an exemplary process system 10 that can utilize side-by-side fluidized beds 12 and 14 where the reaction occurs in a fluidized bed reactor 12 and a fluidized bed heat exchanger 14 is used for heating the reactants and cooling a heat exchange medium passing between 13A and 13B. Each bed includes substantially inert particles adapted to be fluidized in the presence of a moving gas. Bed 14 can further be used for preheating reactant gases 11 from gas source 16. Gas source 16 can include the introduction of separate reactant streams of oxygen and hydrocarbon or a premixed supply. Oxygen can be added at any point prior to the reactor or at the reactor (not shown). The gases leaving bed 14 flow through stream 15 into reactor 12. A circulating heat exchange fluid 13A (cooled leaving bed 14) and 13B (heated leaving reactor 12) can be used to go between the two fluidized beds 12 and 14 as a heat transfer medium. The heat transfer medium does not necessarily interact with the reactant or product streams of the system and typically is only used for heat transfer.

Heat can be transported more efficiently from the reactor 12 to the bed 14 and cooling can be transported more efficiently from the bed 14 to the reactor 12 as compared to traditional systems. The heat transfer coefficient using the fluidized beds can be up to 25 times more efficient than conventional gas-gas heat transfer and in a further embodiment 5-25 times more efficient as compared to traditional systems. This allows for the total surface area of the heat exchanger to be much smaller than would otherwise be possible using traditional heat exchanger systems. Furthermore, since both the hot and cold sides of the system are close to isothermal, the resulting log mean temperature difference will be more favorable for heat exchange design. The reaction products including the desired oxygenate exit the top of reactor 12 (not shown).

FIG. 2 illustrates an alternative example of a fluidized system 20 according to the present disclosure. The fluidized particles themselves 25 are circulated between the hot and cool sides of the system through pathway 27. In this system, a gas source 26 feeds reactants 21 to a fluidized bed heat exchanger 24 before entering the fluidized bed reactor 22 following along flow path 27. This configuration utilizes the diameter of the vessels to influence the gas velocity within bed 24 and reactor 22, respectively. A smaller diameter can selected for bed 24 which will result in an increase in the velocity of the gas 21 and the aerodynamic drag that is applied to the solid particles 25. The particles 25 will then be conveyed with the gas to a lower-pressure area 28 (e.g., a cyclonic or other solid-fluid separator or trap) where the solids 25 can then be collected and funneled into the reactor 22 through path 23A as relatively cooled. After separation from the solids 25, the preheated reactants 21 proceed to the reactor 22 along the path 27. In this manner, there is a constant application of direct cooling. The solids 25 will then mix with the solids already within the reactor 22 and, through gravity (in this example) or other means, will pass from the reactor 22 into the bed 24 as heated through pathway 23B. The reaction products, including the desired oxygenates, are recovered through the top of reactor 22 through product stream 29. Again, the reactant gasses can enter the system as premixed (See FIG. 5). In the same manner, direct heating could be applied to the fluidized bed heat exchanger 24 via pathway 23A by switching it with the reactor 22 and direct cooling would then be applied via pathway 23B (configuration not shown).

FIG. 3 illustrates an example system of a system 30 which includes external thermal management of a fluidized bed reactor 32 according to the present disclosure. In this example, reactor 32 can be analogous to reactors 12 and 22 from FIGS. 1 and 2 and further incorporated into those systems if desired. Alternatively, system 30 can stand alone as the heat entering or being removed from the system can create the desired near isothermal conditions to achieve near complete mixing of reactants. Heat can be removed from the top of the reactor to balance the thermal conditions. A feed stream of premixed reaction gasses 35 can enter reactor 32 coming from a reactant source 36. Product stream 39 is shown having desired oxygenates and other products leaving the top of reactor 32. Additional cooling 33 or additional heating 34 can be provided depending on whether the necessary thermal conditions are met by the reaction inside the reactor. The additional heating 33 or cooling 34 can be applied externally around the reactor, for example via a heating or cooling jacket, or internally within the reactor itself, for example via heating or cooling tubes. The cooling and/or heating sources associated with streams 33 and 34 can incorporate a fluidized medium such as a fluidized bed heat exchanger 14 as shown in FIG. 1 utilizing any fluid medium that would be convenient or advantageous such as downstream products or external liquids for the purposes, among others, of providing heat integration. In a further example, a control system can be implemented that monitors the thermal conditions of the reactor and communicates with the cooling and/or heating sources associated with streams 33 and 34 to cause them to operate to achieve desired thermal conditions within the reactor. For example, if the temperature is too cold to achieve the desired reaction products then the control system can initiate adding heat through heat stream 34 and, likewise, if the reactor temperature becomes too hot, then cooling can be added through stream 33 or alternatively, heat can be removed from the reaction chamber but providing a heat sink or the like.

FIG. 4 illustrates an example reactor system 40 which can be incorporated with the systems described in FIGS. 1-3 if desired. Reactor system 40 includes a reactor 42 analogous to reactors 12, 22, and 32 as described with regard to FIGS. 1, 2, and 3. The reaction product stream, including byproducts, is represented by product stream 49 exiting reactor 42. Product stream 49 can then be fed into recovery system 44 where products can be separated out via product stream 41, along with the separation of inert gas stream 43 and acid gases such as CO2 through acid gas stream 45. Some of the product stream, including any remaining reactants can be fed back into the reactor 42 through recycle stream 47. At least a portion of acid gases, such as carbon dioxide, can be removed from the product stream gases exiting the reactor by absorption, adsorption, membranes, purge, or other means. In a further example methanol produced from the reaction can be used as a solvent to remove at least a portion of carbon dioxide from the gas stream exiting the reactor. In a further example at least a portion of inert gases, such as nitrogen, are removed from the gases exiting the reactor by membranes, purge, or other means. In a further example, the fuel value of the purge stream can be used for on-site utility purposes. In a further example, products can be removed by condensation, adsorption, absorption, or other means.

Figure 5:
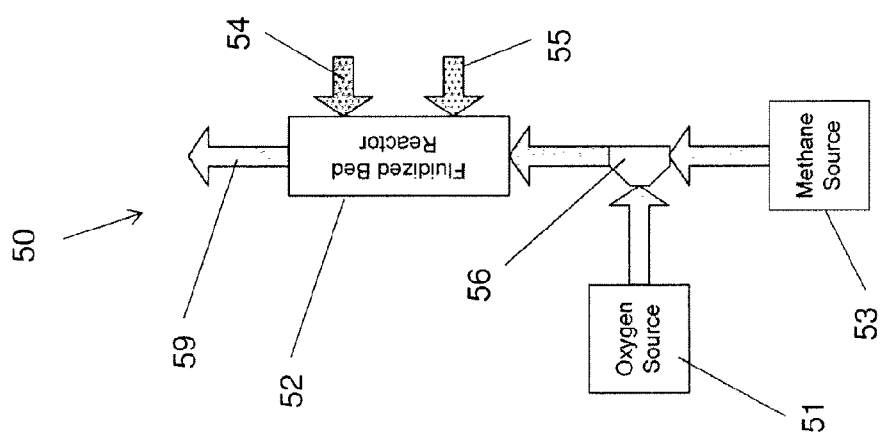
FIG. 5 is a schematic view showing a premixing process of reactants for the direct partial oxidation reaction systems in FIG. 1, FIG. 2 and FIG. 3.

FIG. 5 illustrates an example of a premixing system 50 of the reactant streams which can be incorporated into any of the systems described herein. In this example, system 50 includes an oxygen source 51 and a methane source 53 which delivers oxygen and methane respectively to a mixing means 56 for combining reactant streams prior to preheating or reacting in a fluidized bed reactor 52. In this example, additional heating 55 or cooling 54 can be introduced for heating or cooling the premixed reactants. A product stream 59 exits through the top which can be recycled back into the system for further conversion. Product stream 59 can also be delivered to a recovery system to collect and separate desired products.

Figure 6:
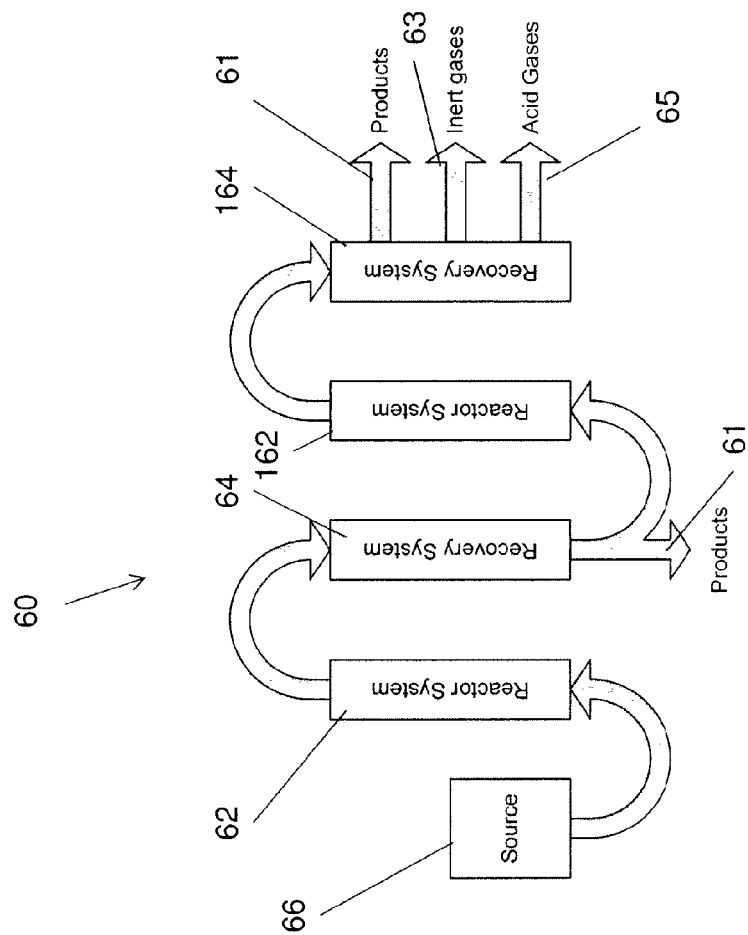
FIG. 6 is a schematic view showing a fourth embodiment of the direct partial oxidation reaction system including reactors and recovery systems in series with one another.

FIG. 6 illustrates a reaction system 60 which includes a series of fluidized bed reactors and recovery systems. In this example, a reactant source 66 delivers reactants to a first reactor system 62. The product stream from reactor 62 is delivered to recover system 64. The desired products are recovered from stream 61 while the remaining components leaving system 64 are delivered to a second reactor system 162 where further conversion of the reactants is achieved. The product from reactor 162 is delivered to a second recovery system 164 which can separate products 61 from inert gas 63 and acid gas 65. This is particularly useful in environments where the source gas contains a mixture of hydrocarbon compounds, such as natural gas which contains methane and ethane as well as higher hydrocarbons. The higher hydrocarbons can often react to produce more methane, making multiple reactors in series advantageous. Multiple reactors in series may also be advantageous because the activation temperature for the reaction of higher hydrocarbon is often lower than for lower hydrocarbons meaning the conditions of each reactor can be changed in order to maximize desired products and conditions. There can be any number of reactors in series as shown in the sequence from reactor 62 to reactor 162.

Figure 9:
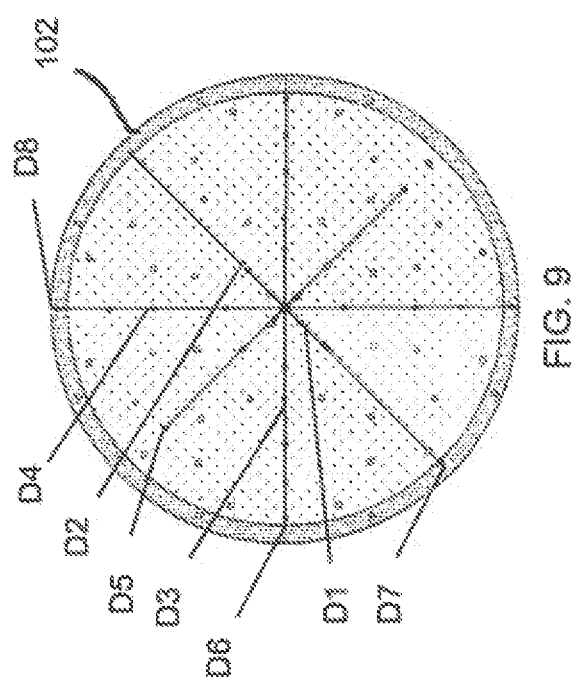
FIG. 9 is a top view of the distributor plate used for distributing the first stream of hydrocarbon gas and the second stream of gas including oxygen.
Figure 10:
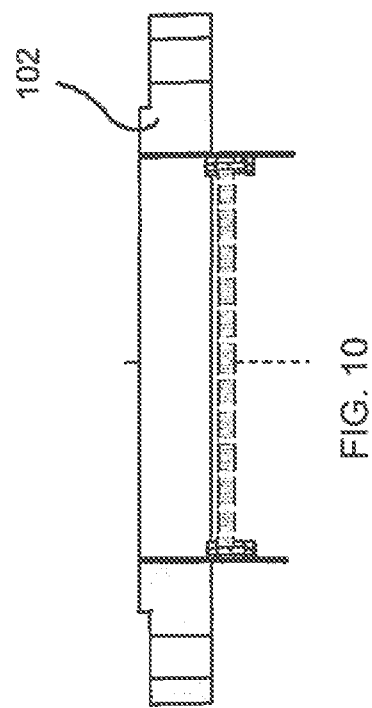
FIG. 10 is a cross-sectional view of the distributor plate.
Figure 11:
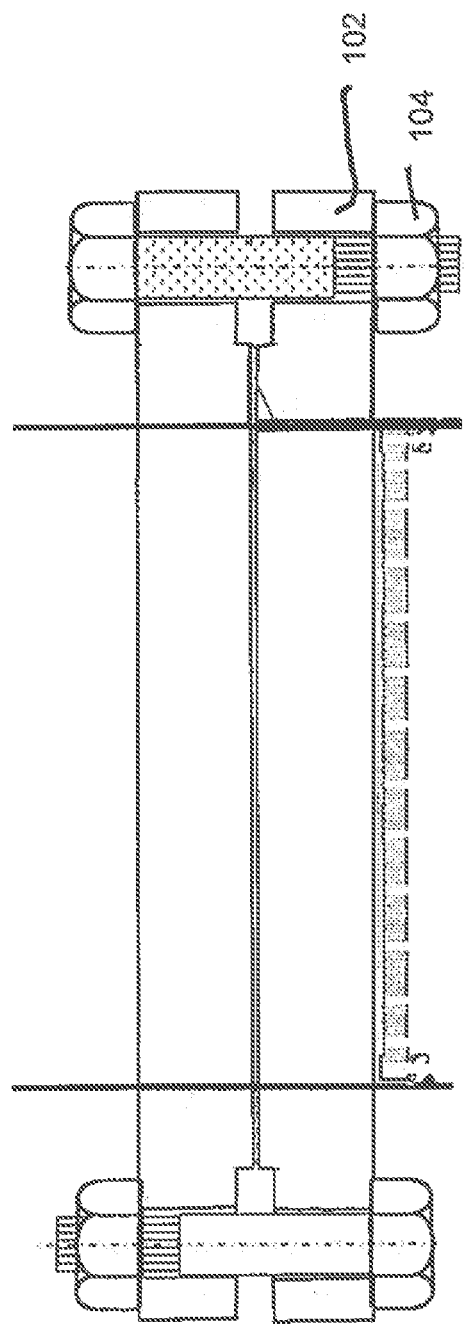
FIG. 11 is a cross-sectional view of the distributor plate and the fluidized bed reactor wherein the distributor plate is fastened to the fluidized bed reactor using a fasteners.
Figure 12:
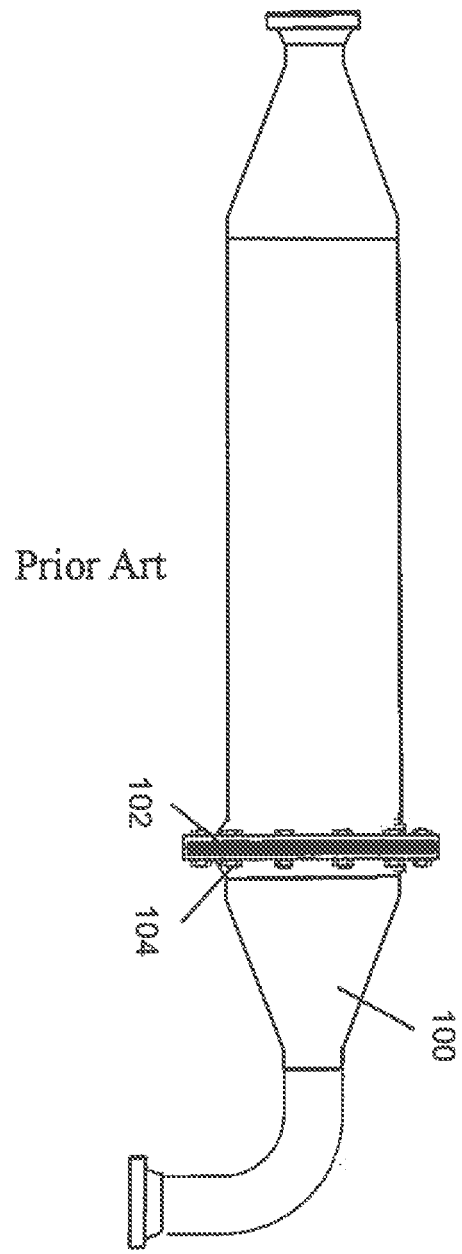
FIG. 12 is an elevation view of the fluidized bed reactor.

FIG. 1 is a schematic diagram that illustrates a first method for making oxygenates from a non-catalytic reaction. The method comprises the first step of mixing a first stream of hydrocarbon gas with a second stream of gas including oxygen in a mixer. Next, a reactant stream is outputted from the mixer including the hydrocarbon gas of the first stream and the second stream of gas including oxygen. The reactant stream is then heated in a heat source, such as a heater or a heat exchanger, to a predetermined temperature range of at least 300° C., preferably between 316° C. and 372° C., and at a pressure of at least 40 atm, preferably between 40 atm and 85 atm, more preferably between 41 atm and 55 atm. If a heat exchanger is used, it may include a first portion used as the heat source. The heated reactant stream is then inputted into a reactor at a point of entry 100, preferably a fluidized bed reactor. As illustrated in FIG. 1, the reactant stream exits the first portion of the heat exchanger at a first temperature range of at least 300° C., preferably at least 316° C. The fluidized bed reactor typically includes a reaction chamber, a distributor plate 102 and a plurality of inert reactor particles in the reaction chamber. If the heat source is a heat exchanger it also includes a second portion at least partially located in the reaction chamber of the fluidized bed reactor. The heated reactant stream is distributed into the reaction chamber of the fluidized bed reactor by feeding the heated reactant stream through the distributor plate 102. The distributor plate 102 having a circular shape includes a plurality of apertures disposed on the distributor plate 102 to allow a thorough mixture between the first stream of hydrocarbon gas and the second stream of gas including oxygen. The apertures may be arranged in a ring shaped fashion having different diameters, such as the illustrated example in FIG. 9, shown as D1 through D8. As illustrated in FIG. 10, a center hole may be included. The distributor plate 102 is fastened to the fluidized bed reactor using fasteners 104 for more efficient heat transfer between the distributor plate 102 and the fluidized bed reactor. Alternatively, the distributor plate 102 may also be welded on to the fluidized bed reactor for providing more efficient heat transfer between the distributor plate 102 and the fluidized bed reactor, preferably configured to at least transfer heat from the distributor plate 102. The inert reactor particles are used to improve heat transfer and consistent temperatures throughout the reaction chamber. As such, the inert particles are fluidized in the reaction chamber by feeding the heated reactant stream vertically through the reaction chamber, which suspends the inert reactor particles in gas in the reaction chamber of the fluidized bed reactor. The distributor plate 102 may be integrated with the second portion of the heat exchanger.

The hydrocarbon gas in the heated reactant stream is oxidized with the gas including oxygen in the reaction chamber of the fluidized bed reactor to produce oxygenates, such as methanol. Throughout the whole oxidation reaction, the fluidized bed reactor is preferably maintained at an isothermal condition or as close to an isothermal condition as possible. For the production of oxygenates, the temperature is usually between 400° C. and 900° C., and to maximize the production of methanol uses an operating temperature range, preferably between 426° C. and 483° C. Similarly, an operating pressure of at least 40 atm, preferably between 40 atm and 85 atm to facilitate with the production of the oxygenates and more preferable for the production of methanol between 41 atm and 55 atm. In order to maintain the isothermal condition in the fluidized bed reactor, a coolant may be cycled between the first portion of the heat exchanger and the second portion of the heat exchanger allowing the fluidized bed reactor to complete the step of heating the reactant stream and further perform a step of cooling the fluidized bed reactor with minimal energy expenditure or also maintaining the desired temperature. In other words, the coolant is cycled between the heat exchanger and the fluidized bed reactor for heating the reactant stream as well as cooling the fluidized bed reactor. Of course, in some instances the heat source will be both a heat exchanger and a heater to provide the desired heat for the step of heating, such as on startup of the progress. Likewise, the reactor may include supplemental cooling methods well known in the art, however, as describe below and to reduce cost, complexity and simplicity controls, the present invention preferably adjusts the temperature by adjusting the volume of oxygen containing gas used. A product stream including the oxygenates, byproducts, and unreacted hydrocarbon gas is outputted from the fluidized bed reactor.

FIG. 2 illustrates an alternative schematic diagram of a second method for making oxygenates from a non-catalytic reaction. As illustrated in FIG. 2, a first stream of hydrocarbon gas and a second stream of gas including oxygen in are mixed a mixer. The mixer outputs a reactant stream including the hydrocarbon gas of the first stream and the second stream of gas including oxygen. The reactant stream is then heated in a heat source, such as a heater or a heat exchanger, to a predetermined temperature range of at least 300° C., preferably between 316° C. and 372° C. for the production of methanol. The pressure is also at least 40 atm, preferably between 40 atm and 85 atm and for the production of methanol, preferably between 41 atm and 55 atm. The heated reactant stream exits the first portion of the heat exchanger. To improve heat transfer, the first portion of the heat exchanger may include inert particles, similar to or the same as the inert particles in the reactor. The inert particles are removed from the reactant the reactant stream. As the reactant stream exits the heat exchanger, it may include fluidized inert particles. The velocity of the reactant stream entering the heat exchanger may be less than the velocity of the reactant stream through the heat exchanger. More specifically, the reactant stream entering the first portion of the heat exchanger has a first velocity and a second velocity in the first portion of the heat exchanger. The velocity increase occurs because the first portion is configured to include a reduced diameter section having a predetermined diameter to increase the velocity of the reactant stream. More specifically, the increased velocity better fluidizes the particles, thereby improving heat transfer. Specifically, the first velocity of the reactant stream is maintained prior to its entry to the first portion of the heat exchanger. Next, the heated reactant stream is forced through the reduced diameter section in the first portion of the heat exchanger to increase the first velocity of the reactant stream to the second velocity that is greater than the first velocity.

The plurality of inert particles may then be preferably removed from the heated reactant stream by passing the heated reactant stream through a particle separator to separate the inert particles from the mixed hydrocarbon gas and gas containing oxygen heated reactant stream before the reactant stream enters the fluidized bed reactor. These inert particles may be fed into the reactor on an opposite side of the distributor plate from the point of entry of the reactant stream into the reaction chamber, and give the lower temperature of the particles as compared to the reactor, such feeding may contribute to the cooling of the reactor. In general, the plurality of inert particles are input into the fluidized bed reactor from the top of the fluidized bed reactor as the gas particles rises from the bottom of the fluidized bed reactor to achieve a favorable fluidization of the inert particles. The feed rate may also be controlled to ensure that the desired temperature is maintained. In some instances, the inert particles could be fed back to the heat exchanger, however, it has been found preferable to feed the particles to the reactor, allow them to heat in the reactor and then feed excess particles from the reactor to the heat exchanger or even particles separated from the product stream, all of which are hotter than the first portion of the heat exchanger. Of course, while the removal of these items does not cool the reaction, it does remove a mass of heated particles, which are then replaced by cooler particles. The heated reactant stream is then inputted into the fluidized bed reactor from the first portion of the heat exchanger at a temperature of at least 300° C., preferably at least 316° C. wherein the fluidized bed reactor includes a reaction chamber, and a plurality of inert reactor particles in the reaction chamber. The heated reactant stream is distributed into the reaction chamber of the fluidized bed reactor by feeding the heated reactant stream through the distributor plate 102. The distributor plate 102 having a circular shape includes a plurality of apertures disposed on the distributor plate 102 to allow a thorough mixture between the first stream of hydrocarbon gas and the second stream of gas including oxygen. The apertures may be arranged in a ring shaped fashion having different diameters, such as the illustrated example in FIG. 9, shown as D1 through D8. The inert reactor particles are fluidized in the reaction chamber by feeding the heated reactant stream vertically through the reaction chamber and suspending the inert reactor particles in the reaction chamber of the fluidized bed reactor. The hydrocarbon gas in the heated reactant stream is oxidized with the gas including oxygen in the heated reactant stream in the reaction chamber of the fluidized bed reactor to produce oxygenates. Throughout the whole oxidation reaction, the fluidized bed reactor is maintained as close as possible to an isothermal condition having an operating temperature range, preferably between 300° C. and 900° C., preferably between 400° C. and to 600° C., most preferably between 426° C. and 483° C. The operating pressure may vary in a relationship with the temperature, however, an operating pressure of at least 40 atm, most preferably between 40 atm and 85 atm facilitates the production of the oxygenates, and 41 atm to 55 atm is preferable for the production of methanol and other desirable oxygenates of the above preferred temperature for the production of methanol.

As stated above, the present invention maintains the isothermal conditions within the fluidized bed reactor by inputting the inert particles separated from the reactant stream into the reaction chamber of the fluidized bed reactor to cool the fluidized bed reactor. The inert reactor particles in the fluidized bed reactor may also be transferred to the heat exchanger for heating the first portion of the heat exchanger. A medium such as a coolant may be cycled between the first portion and the second portion of the heat exchanger to heat the first portion of the heat exchanger and to cool the second portion in the reaction chamber, thereby helping maintain the isothermal condition as well as to maximize the energy efficiency by transferring heat from the exothermic reaction to the reactant stream.

FIG. 4 is a schematic diagram illustrating a recovery system used in connection with the schematic diagrams set forth in FIGS. 1 and 2. Specifically, FIG. 4 discloses a step of isolating the oxygenates in the product stream from the byproducts and the unreacted reactants by feeding the product stream through a first recovery system that separates the product stream into oxygenates and a recycle stream including any byproduct and any unreacted hydrocarbon gas that leaves the reactor as part of the product stream. Preferably the recovery system is efficient at providing a recycle stream which is free of oxygenates, but of course some oxygenates may remain. Therefore, the recycle stream is considered free or substantially free of oxygenates even if some oxygenates are left. The byproducts are removed from the recycle stream. Many times these by products have commercial value and may be captured and commercially sold. The unreacted hydrocarbon gas is then recycled to the fluidized bed reactor by inputting the recycle stream containing the unreacted hydrocarbon gas back into the fluidized bed reactor.

FIG. 6 is a schematic diagram illustrating a recovery system used in connection with the schematic diagrams set forth in FIGS. 1 and 2. Specifically, FIG. 6 discloses a step of inputting the recycle stream to a second fluidized bed reactor having a second reaction chamber and oxidizing the unreacted hydrocarbon gas in the recycle stream in the second reaction chamber of the second fluidized bed reactor to produce oxygenates. Next, a second product stream is outputted from the second fluidized bed reactor wherein the second product stream includes oxygenates, byproducts and unreacted hydrocarbon gas. The oxygenates from the second product stream are isolated from the second product stream by inputting the second product stream through a second recovery system and separating the oxygenates from the byproducts and the unreacted hydrocarbon gas in the second product stream. This recycling may be repeated again. Of course, the recycle stream could be input into the first reactor or some other variation. Also, variations from any of the systems described in relation with the figures could be added to any other described system in another figure.

Figure 7:
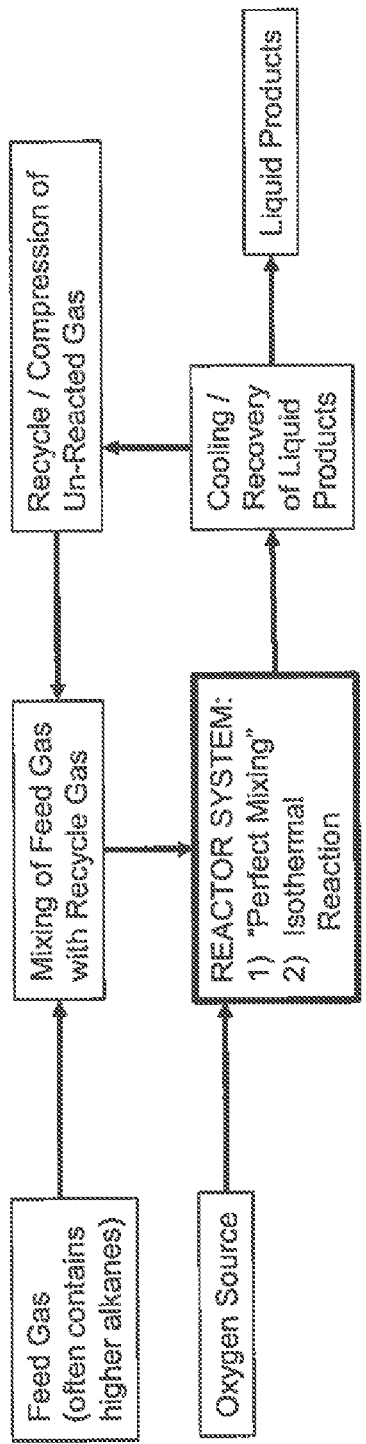
FIG. 7 is a schematic view showing a fifth embodiment of the direct partial oxidation reaction system.

FIG. 7 is a schematic diagram illustrating a third method for making oxygenates from a non-catalytic reaction. Specifically, FIG. 7 illustrates a first step of feeding a first stream of hydrocarbon gas into a mixer. Next, a recycle stream from a recovery system is also fed into the mixer. The first stream and the recycle stream are thoroughly mixed in the mixer to output a combined stream. The combined stream is then heated to a first predetermined temperature of at least 300° C. through a heat source and wherein the combined stream is fed to the heat source at a pressure of at least 40 atm, preferably between 40 atm and 85 atm, most preferably between 41 atm and 55 atm. The heat source could be a heater, a heat exchanger or some combination. Next, the heated combined stream is inputted into a fluidized bed reactor having a reaction chamber and a plurality of reactor particles in the reaction chamber. A second stream of gas including oxygen is separately inputted into the fluidized bed reactor at a second predetermined temperature between 20° C. and 300° C., preferably 20° C. and 120° C., most preferably between 38° C. and 93° C. The volume of the second stream inputted into the fluidized bed reactor is controlled based on the internal temperature of the fluidized bed reactor and more specifically controlled to maintain as close as possible to an isothermal reaction. The concentration of the gas including oxygen may be monitored by including an $O_2$ sensor inside the reactor. In order to accurately measure the temperature and pressure inside the reactor, a plurality of pressure and temperature may be used in the reactor for providing an accurate temperature and pressure measurement inside the reactor.

The inert reactor particles are fluidize in the fluidized bed reactor by feeding the heated combined stream and the second stream through the reaction chamber and suspending the inert reactor particles in the reaction chamber of the fluidized bed reactor. The hydrocarbon gas in the heated combined stream and the second stream of gas including oxygen are oxidized in the reaction chamber of the fluidized bed reactor to produce oxygenates. The flow rate of the second stream of gas including oxygen is varied to maintain the fluidized bed reaction at an isothermal condition having an operating temperature between 300° C. and 900° C., preferably between 400° C. and 600° C., most preferably between 426° C. and 483° C., particularly when producing methanol and the like. A product stream is outputted from the fluidized bed reactor including the oxygenates, byproducts, and unreacted hydrocarbon gas. The oxygenates are isolated from the product stream by sending the product stream through the recovery system configured to separate the oxygenates in the products stream from the recycle stream which include the byproducts and the unreacted hydrocarbon gas. Finally, the byproducts and the unreacted hydrocarbon gas from the product stream are cycled to the mixer for allowing the recycle stream to mix with the first stream of hydrocarbon gas. Of course, the recycle stream could also be fed into the reactor or a second reactor.

Figure 8:
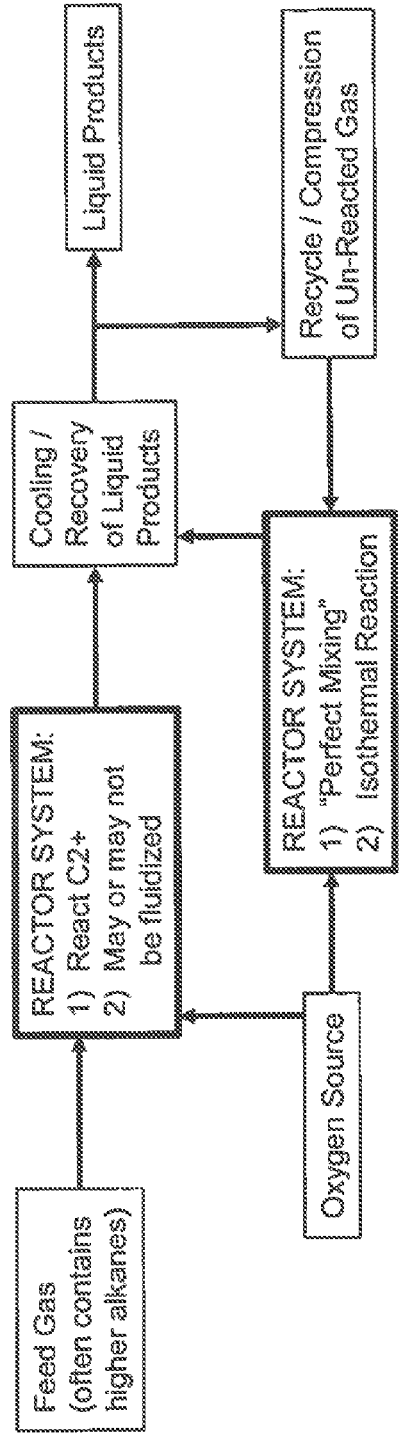
FIG. 8 is a schematic view showing a sixth embodiment of the direct partial oxidation reaction system including a pre-reaction step where incoming hydrocarbon gases from a feed source can be reacted separately from the hydrocarbon gas in the recovery system.

FIG. 8 is a schematic diagram illustrating a fourth method for making oxygenates from a non-catalytic reaction. Specifically, FIG. 8 illustrates a first step of compressing a first stream including a hydrocarbon gas to a predetermined pressure of at least 40 atm, preferably between 40 atm and 85 atm, most preferably between 41 atm and 55 atm. The compressed first stream is heated to a first predetermined temperature range of at least 300° C., preferably between 300° C. and 900° C., more preferably 310° C. and 600° C., and most preferably between 316° C. and 372° C., by feeding the compressed first stream through a heat source. The heat source could be a heater or a heat exchanger or some combination. Next, the heated and compressed first stream is inputted into a first reactor having a first reaction chamber. A gas including oxygen at a second predetermined temperature of at least 30° C., preferably between 30° C. and 120° C., most preferably between 36° C. and 96° C., is inputted into the first reaction chamber having a first reaction chamber volume. The first reactor operates at a first reactor temperature and a first reactor pressure. The gas including oxygen is fed into the first reaction chamber of the first reactor at a rate to control the pressure and temperature in the first reaction chamber to oxidize primarily ethane. The hydrocarbon gas of the heated and compressed first stream is oxidized with the second stream of gas including oxygen in the first reaction chamber to produce oxygenates. In the first reactor, the direct partial oxidation primarily focuses on the breaking of C—C bonds in ethane which in turn produces methane as a product. A product stream is outputted from the first reactor including the oxygenates, byproducts and unreacted hydrogen gas including methane. The oxygenates are isolated from the product stream with a recovery system separating the oxygenates from a recycle stream having the byproducts and the unreacted hydrocarbon gas.

The recycle stream is then inputted into a second reactor having a second reaction chamber wherein the second reactor is a fluidized bed reactor including a plurality of inert reactor particles in the second reaction chamber. The second stream of gas including oxygen at the second predetermined temperature of at least 30° C., preferably between 30° C. and 120° C., most preferably between 36° C. and 96° C., is also inputted into the second reactor having a second reaction chamber volume wherein the first reactor chamber volume is smaller than the second reactor chamber volume. The second reactor operates at a second reactor temperature and a second reactor pressure wherein the first reactor temperature is less than the second reactor temperature and the first reactor pressure is less than the second reactor pressure. The second stream of gas is inputted into the second reaction chamber of the second reactor at a rate to control pressure and temperature in the second reaction chamber to oxidize primarily with methane. The inert reactor particles in the second reactor chamber is fluidized by feeding the recycle stream and the second stream of gas including oxygen through the second reaction chamber and suspending the inert reactor particles in the second reaction chamber of the second fluidized bed reactor. The unreacted hydrocarbon gas in the recycle stream including methane is oxidized with the second stream of gas including oxygen in the second reaction chamber of the reactor to produce methanol.

A second product stream is outputted from the second reactor including the oxygenates, byproducts, and unreacted hydrocarbon gas. The oxygenates from the second product stream is isolated from the byproducts and the unreacted hydrocarbon gas of the second product stream with the recovery system. The recovery system includes a first separator for separating the oxygenates from the product stream and a second separator for separating the oxygenates from the second product stream.

As used herein, oxygen containing gas is any gas that includes oxygen, such as but not limited to $O_2$, and $NO_2$ gases, or even compressed air. However, because the oxygen containing gas is to be reacted with a hydrocarbon, substantially pure CO or $CO_2$ is not desirable.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility.

What is claimed is:

1. A method for making oxygenates using a non-catalytic reaction, said method comprising the steps of:
    mixing a first stream of hydrocarbon gas with a second stream of gas including oxygen in a mixer;
    outputting a reactant stream from the mixer including the hydrocarbon gas of the first stream and the second stream of gas including oxygen;
    providing a heat exchanger having a first portion and a second portion, wherein the second portion is at least partially located in a reaction chamber of a fluidized bed reactor;
    heating the reactant stream to a predetermined temperature of at least 300° C. and a pressure of from 40 to 85 atm to form a heated reactant stream in the heat exchanger and feeding the heated reactant stream to the fluidized bed reactor from the first portion of the heat exchanger at a temperature of 300 to 372° C. at a point of entry into the fluidized bed reactor;
    inputting the heated reactant stream into the fluidized bed reactor and wherein the fluidized bed reactor reaction chamber includes a plurality of inert reactor particles in the reaction chamber;
    distributing the heated reactant stream into the reaction chamber of the fluidized bed reactor by sending the heated reactant stream through a distributor plate,
    fluidizing the inert reactor particles in the reaction chamber by feeding the heated reactant stream vertically through the reaction chamber and suspending the inert reactor particles in the reaction chamber of the fluidized bed reactor;
    oxidizing in the reaction chamber of the fluidized bed reactor the hydrocarbon gas in the heated reactant stream with the gas including oxygen in the heated reactant stream to produce oxygenates comprising at least one of methanol, ethanol and propanol;
    maintaining the fluidized bed reactor at an isothermal condition of ±10% of a desired operating temperature range of from 300 to 900° C. and a desired operating pressure of 40 to 85 atm to facilitate the production of the oxygenates and further including a step of cycling inert reactor particles from the reaction chamber through the heat exchanger thereby allowing the fluidized bed reactor to complete said step of heating said reactant stream and to further perform a step of cooling the fluidized bed reactor with minimal energy expenditure as part of said step of maintaining the fluidized bed reactor at an isothermal condition; and
    outputting a product stream including the oxygenates, byproducts, and unreacted hydrocarbon gas from the fluidized bed reactor.

2. A method as set forth in claim 1 wherein the heated reactant stream exiting the first portion of the heat exchanger includes a plurality of inert particles and further including the step of removing the plurality of inert particles from the reactant stream.

3. A method as set forth in claim 2 further including a step of accelerating the heated reactant stream having a first velocity before the first portion of the heat exchanger and a second velocity in the first portion of the heat exchanger in the heat exchanger.

4. A method as set forth in claim 3 wherein said step of accelerating the heated reactant stream in the heat exchanger further including the step of maintaining the first velocity with the heated reactant stream and wherein the heated reactant stream is forced through a reduced diameter section in the first portion of the heat exchanger to increase the first velocity of the reactant stream to the second velocity that is greater than the first velocity.

5. A method as set forth in claim 2 wherein said step of removing the plurality of inert particles from the heated reactant stream occurs by transferring the heated reactant stream through a particle separator to separate the inert particles from the heated reactant stream, before the reactant stream enters the fluidized bed reactor.

6. A method as set forth in claim 5 further including a step of inputting the inert particles removed from the heated reactant stream by the particle separator into the reaction chamber of the fluidized bed reactor, on an opposite side of the distributor plate from the point of entry of the reactant stream into the reactor chamber.

7. A method as set forth in claim 6 wherein said step of inputting the inert particles cools the reaction chamber.

8. A method as set forth in claim 7 further including the step of cycling a coolant between the first portion and the second portion of the heat exchanger to heat the first portion of the heat exchanger and to cool the second portion in the reaction chamber.

9. A method as set forth in claim 1 further including a step of isolating the oxygenates in the product stream from the byproducts and the unreacted hydrocarbon gas by feeding the product stream through a first recovery system that separates the product stream into oxygenates and a recycle stream including the byproducts and the unreacted hydrocarbon gas.

10. A method as set forth in claim 9 further including a step of removing the byproducts from the recycle stream.

11. A method as set forth in claim 10 further including a step of recycling the unreacted hydrocarbon gas from the first recovery system, after said step of removing the byproducts from the recycle stream, to the fluidized bed reactor by inputting the recycle stream into the fluidized bed reactor.

12. A method as set forth in claim 9 further including a step of inputting the recycle stream to a second fluidized bed reactor having a second reaction chamber and oxidizing the unreacted hydrocarbon gas in the recycle stream in the second reaction chamber of the second fluidized bed reactor to produce oxygenates.

13. A method as set forth in claim 12 further including a step of outputting a second product stream from the second fluidized bed reactor and wherein the second product stream includes oxygenates, byproducts and unreacted hydrocarbon gas.

14. A method as set forth in claim 13 further including a step of isolating the oxygenates from the second product stream by inputting the second product stream through a second recovery system and separating the oxygenates from the byproduct and the unreacted hydrocarbon gas in the second product stream.

15. A method as set forth in claim 1 wherein said step of maintaining uses the operating temperature between 426° C. and 483° C.

16. A method as set forth in claim 1 wherein the reactant stream in said step of heating is at the predetermined temperature of between 316° C. and 372° C.

17. A method as set forth in claim 1 wherein the distributor plate includes a plurality of apertures to allow for mixing of the first stream of hydrocarbon gas and the second stream of gas including oxygen.

18. A method for making oxygenates using a non-catalytic reaction, said method comprising the steps of:
    feeding a first stream of hydrocarbon gas into a mixer;
    feeding a recycle stream from a recovery system into the mixer;
    mixing the first stream and the recycle stream in the mixer to output a combined stream;
    heating the combined stream to a first predetermined temperature of from 300 to 372° C. by feeding the combined stream through a heat source and wherein the combined stream is fed to the heat source at a pressure of 40 to 85 atm;
    inputting the heated combined stream from the heat source into a fluidized bed reactor having a reaction chamber and a plurality of inert reactor particles in the reaction chamber;
    inputting a second stream of gas including oxygen at a second predetermined temperature which is lower than the first predetermined temperature to the fluidized bed reactor separately from the heated combined stream;
    controlling the volume of the second stream inputted into the fluidized bed reactor based on the internal temperature of the fluidized bed reactor;
    distributing the heated reactant stream into the reaction chamber of the fluidized bed reactor by sending the heated reactant stream through a distributor plate,
    fluidizing the inert reactor particles in the fluidized bed reactor by feeding the heated combined stream and the second stream through the reaction chamber and suspending the inert reactor particles in the reaction chamber of the fluidized bed reactor;
    oxidizing the hydrocarbon gas in the heated combined stream with the second stream of gas including oxygen in the reaction chamber of the fluidized bed reactor to produce oxygenates comprising at least one of methanol, ethanol, and propanol;
    varying the flow rate of the second stream to maintain the fluidized bed reactor at an isothermal condition of ±10% of a desired operating temperature between 300° C. and 900° C. and an operating pressure of 40 to 85 atm to facilitate with the production of the oxygenates;
    outputting a product stream including the oxygenates, byproducts, and unreacted hydrocarbon gas from the fluidized bed reactor;
    isolating the oxygenates from the product stream by sending the product stream through the recovery system, the recovery system configured to separate the oxygenates in the product stream from the recycle stream which includes the byproducts and the unreacted hydrocarbon gas; and
    cycling the byproducts and the unreacted hydrocarbon gas from the product stream by sending the recycle stream to the mixer.

19. A method as set forth in claim 18 wherein said step of varying is at the operating temperature between 400° C. and 600° C.

20. A method as set forth in claim 19 wherein said step of varying is at the operating temperature between 426° C. and 483° C.

21. A method as set forth in claim 18 wherein said step of inputting the second stream of gas including oxygen is at the second predetermined temperature between 20° C. and 300° C.

22. A method as set forth in claim 21 wherein said step of inputting the second stream of gas including oxygen is at the second predetermined temperature between 30° C. and 120° C.

23. A method as set forth in claim 22 wherein said step of inputting the second stream of gas including oxygen is at the second predetermined temperature between 38° C. and 93° C.

24. A method as set forth in claim 18 wherein the heat source is one of a heater and a heat exchanger.

25. A method as set forth in claim 18 wherein the combined stream enters the heat source in said step of heating at the pressure between 41 atm and 55 atm.

26. A method as set forth in claim 18 wherein the distributor plate includes a plurality of apertures to allow for mixing of the first stream of hydrocarbon gas and the second stream of gas including oxygen.

27. A method for making oxygenates using a non-catalytic reaction, said method comprising the steps of:
    compressing a first stream including a hydrocarbons gas to a predetermined pressure of 40 to 85 atm;
    heating the compressed first stream to a first predetermined temperature of at least 300° C. by feeding the compressed first stream through a heat source;
    inputting the heated and compressed first stream from the heater into a first reactor having a first reaction chamber;
    inputting a gas including oxygen at a second predetermined temperature, said second predetermined temperature lower than said first predetermined temperature, into the first reaction chamber of the first reactor and separately from the heated stream;
    oxidizing the hydrocarbon gas of the heated and compressed first stream with the second stream of gas including oxygen in the first reaction chamber of the first reactor to produce oxygenates comprising at least one of methanol, ethanol, and propanol;

outputting a product stream including the oxygenates, byproducts and unreacted hydrocarbon gas from the first reactor;

isolating the oxygenates from the product stream with a recovery system separating the oxygenates from a recycle stream having the byproducts and the unreacted hydrocarbon gas;

heating and compressing the recycle stream to a temperature of at least 300° C. and a pressure of from 40 to 85 atm and then inputting the recycle stream into a second reactor having a second reaction chamber;

inputting a second stream of gas including oxygen at the second predetermined temperature to the second reactor separately from the recycle stream;

oxidizing the unreacted hydrocarbon gas in the recycle stream with the second stream of gas including oxygen in the second reaction chamber of the second reactor under isothermal conditions of ±10% of a desired operating temperature range of from 300 to 900° C. in said second reaction chamber at a pressure of from 40 to 85 atm to produce oxygenates comprising at least one of methanol, ethanol, and propanol;

outputting a second product stream including the oxygenates, byproducts and unreacted hydrocarbon gas from the second reactor; and isolating the oxygenates from the second product stream with the recovery system separating the oxygenates from the byproducts and the unreacted hydrocarbon gas of the second product stream.

28. A method as set forth in claim 27 wherein the second reactor is a fluidized bed reactor including a plurality of inert reactor particles in the second reaction chamber.

29. A method as set forth in claim 28 further including the step of fluidizing the inert reactor particles in the fluidized bed reactor by feeding the recycle stream and the second stream through the reaction chamber and suspending the inert reactor particles in the second reaction chamber of the second fluidized bed reactor.

30. A method as set forth in claim 27 wherein said step of isolating the oxygenates from the product stream includes using a first separator of the recovery system and said step of isolating the oxygenates from the second products stream includes using a second separator of the recovery system.

31. A method as set forth in claim 27 wherein said first stream is compressed to the predetermined pressure between 41 to 55 atm.

32. A method as set forth in claim 27 wherein said recycle stream is compressed a pressure between 41 atm and 55 atm.

33. A method as set forth in claim 27 wherein in said step of heating the compressed first stream is heated to a first predetermined temperature between 300° C. and 900° C.

34. A method as set forth in claim 33 wherein in said step of heating the compressed first stream is heated to a first predetermined temperature between 310° C. and 600° C.

35. A method as set forth in claim 34 wherein in said step of heating the compressed first stream is heated to a first predetermined temperature between 316° C. and 372° C.

36. A method as set forth in claim 27 wherein in said step of inputting the gas including oxygen said second predetermined temperature is at least 30° C.

37. A method as set forth in claim 36 wherein in said step of inputting the gas including oxygen said second predetermined temperature is between 30° C. and 120° C.

38. A method as set forth in claim 37 wherein in said step of inputting the gas including oxygen said second predetermined temperature is between 36° C. and 96° C.

39. A method as set forth in claim 27 wherein the first reactor operates at a first reactor temperature and a first reactor pressure and the second reactor operates at a second reactor temperature and a second reactor pressure and wherein the first reactor temperature is less than the second reactor temperature.

40. A method as set forth in claim 27 wherein the first reactor operates at a first reactor temperature and a first reactor pressure and the second reactor operates at a second reactor temperature and a second reactor pressure and wherein the first reactor pressure is less than the second reactor pressure.

41. A method as set forth in claim 27 wherein the first reactor has a first reaction chamber volume and the second reactor has a second reactor chamber volume and wherein the first reactor chamber volume is smaller than the second reactor chamber volume.

42. A method as set forth in claim 27 wherein said step of inputting a gas including oxygen in the first reaction chamber further includes the step of feeding the gas including oxygen at a rate to control the pressure and temperature in the reaction chamber of the first reactor to oxidize primarily ethane, and wherein said step of inputting a gas including oxygen in the second reaction chamber includes the step of feeding the gas including oxygen at a rate to control the pressure and temperature in the reaction chamber of the second reactor to oxidize primarily methane.

* * * * *